United States Patent [19]

Oosaka

[11] Patent Number: 4,731,334
[45] Date of Patent: Mar. 15, 1988

[54] METHOD AND APPARATUS FOR DETECTING AND QUANTITATIVELY DETERMINING SELENIUM

[75] Inventor: Hajime Oosaka, Osaka, Japan

[73] Assignee: Sumitomo Electric Industries, Ltd., Osaka, Japan

[21] Appl. No.: 811,760

[22] Filed: Dec. 20, 1985

[30] Foreign Application Priority Data

Jan. 9, 1985 [JP] Japan .................................. 60-941
Jan. 9, 1985 [JP] Japan .................................. 60-942

[51] Int. Cl.[4] ..................... G01N 21/62; G01N 33/20
[52] U.S. Cl. ..................................... 436/73; 436/171; 436/173; 436/182; 356/437
[58] Field of Search ............. 436/73, 182, 171; 356/437, 314; 422/83

[56] References Cited

U.S. PATENT DOCUMENTS 3,898,501  8/1975  Hosoya et al. .................. 356/314 X
4,309,385  1/1982  Harada et al. ........................ 422/83

FOREIGN PATENT DOCUMENTS 769425  10/1980  U.S.S.R. ............................... 436/73

OTHER PUBLICATIONS

Goulden et al., Analytical Chemistry, 46(11), pp. 1431-1436.
Jordanov et al., Talanta, 21(11), pp. 1217-1219.
Terada et al., Talanta, 22(1), pp. 41-49.
Golembeski, Talanta, 22(6), pp. 547-549.
Bédard et al., Can. J. Spectrosc., 21(3), pp. 64-68.
Durig et al., J. Mol. Spectrosc., 64, pp. 474-490.
Egaas et al., Atomic Absorption Newsletter, 17(6), pp. 135-138.
Reamer et al., Analytical Chemistry, 53, pp. 1192-1195.
Dittrich et al., Spectrochimica Acia, 39B(2/3), pp. 349-363.

Primary Examiner—Barry S. Richman
Assistant Examiner—Jill Johnston
Attorney, Agent, or Firm—Wenderoth, Lind & Ponack

[57] ABSTRACT

Gaseous selenium is detected and quantitatively determined at a temperature lower than the temperatures employed in the atomic absorption spectroscopic analysis method of the prior art. This is achieved by directing a spectrum line with a wavelength of 335 nm or by two or more spectrum lines having wavelengths of 324 nm, 326 nm, 328 nm, 330 nm, 332.5 nm, 335 nm, 337.5 nm, 340 nm, 342 nm, 344.5 nm, 347 nm, 350 nm, 352.5 nm, 355 nm, 357.3 nm and 360 nm upon gaseous selenium at a temperature of lower than the atomizing temperature of selenium, measuring the absorption of the incident spectrum line by the gaseous selenium and detecting and quantitatively determining the selenium from the peak height of this intensity.

5 Claims, 6 Drawing Figures

METHOD AND APPARATUS FOR DETECTING AND QUANTITATIVELY DETERMINING SELENIUM

BACKGROUND OF THE INVENTION

1. Field of the Invention

This invention relates to a method of detecting and quantitatively determining selenium and a monitor therefor, and more particularly, it is concerned with a method of detecting quantitatively determining gaseous selenium at temperatures lower than that in the atomic absorption spectroscopic analysis of the prior art, and a monitor apparatus therefor.

2. Description of the Prior Art

High sensitivity detection and quantitative determination of selenium is now being required as a result of the development of various compounds containing selenium in various fields of the industry, for example, in the production of semiconductors, alloys, ceramics and glass. For this requirement, the atomic absorption spectroscopic analysis method has hitherto been carried out comprising atomizing selenium at high temperatures, e.g. 2000° C. or higher and then detecting the atomic absorption spectrum characteristic of selenium. The atomic absorption spectrum of selenium has a sharp peak at a wavelength of 196.03 nm, as shown in FIG. 5 (quoted from Catalogue of Hamamatsu Photonics KK). The general structure of an apparatus for the atomic absorption spectroscopic analysis utilizing this peak according to the prior art is as shown in FIG. 6 in which a light from light source 1 is caused to enter and pass through part 2 of of an atomized sampl, then to pass through photoselective means 3, such as a monochromator, and finally to enter photometric means 4–6 comprising a detector 4, and amplifier 5 and a metering part 6, where the light is detected and determined quantitatively. In part 2 relating to an ized sample, an atomizing temperature of 2000° C. or higher is required for atomizing selenium and to this end, a flame is generally used as a convenient method.

However, the above described method of detecting selenium by utilizing an atomic absorption spectrum requires such a high temperature (atomizing temperature) that it is not suitable for detecting selenium at a temperature below the atomizing temperature. That is, for gaseous SeX at a temperature lower than the atomizing temperature, there is no method for detecting and quantitatively determining it, nor is there a monitor for detecting and quantitatively determining it, in situ.

SUMMARY OF THE INVENTION

It is an object of the present invention to provide a method of detecting and quantitatively determining selenium, whereby the above described disadvantages of the prior art can be overcome.

It is another object of the present invention to provide a new method for detecting and determining quantitatively determining selenium, whereby high sensitivity detection and quantitative determination of selenium can be carried out at a temperature lower than the atomizing temperature, which have hitherto been impossible by prior art methods.

It is a further object of the present invention to provide a selenium monitor for detecting and quantitatively determining selenium from the peak height of the intensity of a spectrum line passing through gaseous Se.

These objects can be attained by a method of detecting and quantitatively determining selenium, which comprises making incident a spectrum line with a wavelength of 335 nm or two or more of spectrum lines with wavelength of 324 nm, 326 nm, 328 nm, 330 nm, 332.5 nm, 337.5 nm, 340 nm, 342 nm, 344.5 nm, 347 nm, 350 nm, 352.5 nm, 355 nm, 357.3 nm, and 360 nm upon gaseous selenium at a temperature lower than the atomizing temperature of selenium, measuring the absorption of the above described incident spectrum lines by the above described gaseous selenium and detecting and quantitatively determining selenium from the peak heights of the intensity. The detection is achieved by means of a selenium monitor comprising a furnace or cell provided with heating means and window portions, one of which is connected with means of emitting spectrum lines of wavelengths of 324 nm, 326 nm, 328 nm, 330 nm, 332.5 nm, 335 nm, 337.5 nm, 340 nm, 342 nm, 344.5 nm, 347 nm, 350 nm, 352.5 nm, 355 nm, 357.5 nm and 360 nm and another of which is connected with means of detecting and quantitatively determining selenium from the peak heights of the intensity of the above described spectrum lines passing through gaseous selenium in the furnace or cell provided with heating means.

BRIEF DESCRIPTION OF THE DRAWINGS

The accompanying drawings are designed to illustrate the principle and merits of the invention in greater detail.

DETAILED DESCRIPTION OF THE INVENTION

The inventor has made various efforts to solve the above described problems of the prior art and consequently, has reached the present invention consisting in detecting and quantitatively determining selenium by utilizing the absorption spectrum of gaseous selenium.

That is to say, the present invention provides a method of detecting and quantitatively determining selenium, which comprises making incident a spectrum line with a wavelength of 335 nm or two or more of spectrum lines with wavelengths of 324 nm, 326 nm, 328 nm, 330 nm, 332.5 nm, 335 nm, 337.5 nm, 340 nm, 342 nm, 344.5 nm, 347 nm, 350 nm, 352.5 nm, 355 nm, 357.5 nm and 360 nm upon gaseous selenium at a temperature lower than the atomizing temperature of selenium, measuring the absorption of the incident spectrum lines by the gaseous selenium and effecting detection and quantitative determination of selenium from the peak heights of the intensity. Also provided is apparatus for detecting and quantitatively determining selenium, which comprises a furnace or cell provided with a heating means and window portions in the progress direction of light, one of which has window portions connected with a means of emitting spectrum lines with wavelengths of 324 nm, 326 nm, 328 nm, 330 nm, 332.5 nm, 335 nm, 337.5 nm, 340 nm, 342 nm, 344.5 nm, 347 nm, 350 nm, 352.5 nm, 355 nm, 357.5 nm and 360 nm and another which has window portions connected with a photo-receiving and metering means for detecting and quantitatively determining selenium from the peak heights of the intensity of the spectrum lines passing through gaseous selenium in the furnace or cell provided with heating means.

The method and apparatus of the present invention will now be illustrated in detail by the accompanying drawings.

Selenium is in a gaseous state and is considered to exist as $Se_2$, $Se_4$, $Se_6$ and the like at a temperature lower than the atomizing temperature, particularly 220° to 1000° C., more particularly 220° to 695° C., but this is not identified (Cf. O. Kubaschewski "Metallurgical Thermochemistry" Pergamonpress (1967)).

Figure 1:
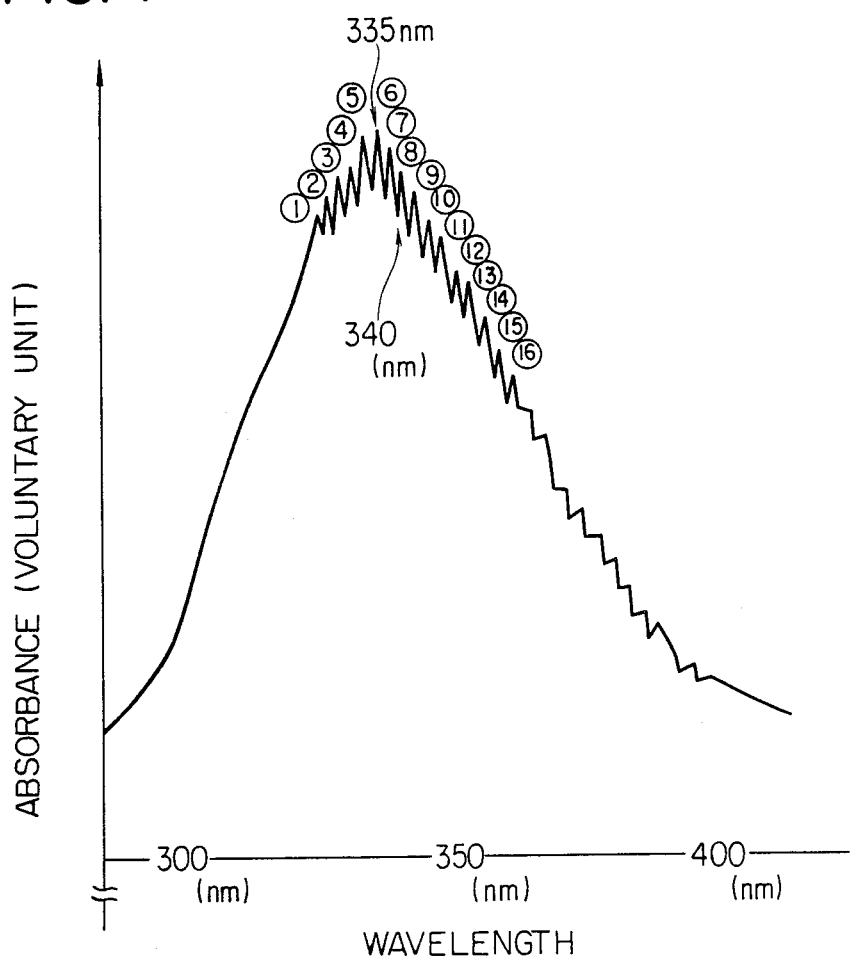
FIG. 1 is an absorption spectrum of gaseous selenium at 450° C., in which the numbers 1 to 16 represent peaks.

The inventor has found total 16 absorption spectra designated as 1 to 16 in FIG. 1 in respect to this gaseous Se. In FIG. 1, the ordinate shows the absorbance (voluntary unit) and the abscissa shows the wavelength (nm). The wavelengths of the peaks numbered 1 to 16 are as follows:

1: 324 nm, 2: 326 nm, 3: 328 nm, 4: 330 nm, 5: 332.5 nm, 6: 335 nm, 7: 337.5 nm, 8: 340 nm, 9: 342 nm, 10: 344.5 nm, 11: 347 nm, 12: 350 nm 13: 352.5 nm, 14: 355 nm, 15: 357.5 nm 16: 360 nm

In the absorption spectrum of FIG. 1, the sixth peak at a wavelength of 335 nm is highest.

The present invention is characterized in that selenium is detected with a high sensitivity by selecting the peak at a wavelength of 335 nm or two or more peaks from the above described peaks 1 to 16 and simultaneously measuring them.

Figure 2:
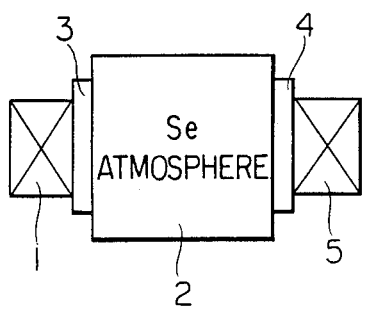
FIG. 2 is a schematic view to illustrate a method of detecting and quantitatively determining selenium according to the present invention.

In principle, the method of detecting and quantitatively determining selenium according to the present invention can be carried out by an apparatus exemplified in FIG. 2. Referring to FIG. 2, emitting part 1 emits a light corresponding to the wavelength of an object peak to be measured in respect to the above described peaks 1 to 16 of gaseous selenium. For example, the emitting part 1 consists of a light source of a hollow-cathode lamp provided with filters each having a center corresponding to each of the spectrum lines 1 to 16. Sample chamber 2 is a furnace or cell provided with a heating means, which has a structure capable of holding selenium gas inside; a window 3 permitting an incident light from emitting part 1 and another window 4 permitting the transmitted light after being absorbed by the selenium gas to be directed to the subsequent photo-receiving part 5 comprising an ordinary monochromator, a detector, an amplifier and a meter.

The principle of the method of detecting and quantitatively determining selenium according to the present invention resides in the fact that a peak absorption as shown in peak nos. 1 to 16 of FIG. 1 can be obtained in proportion to the concentration of gaseous selenium. When the intensity of an incident light upon a sample chamber is represented by I, the intensity of the transmitted light after being absorbed by the gaseous selenium is represented by I, the absorption of the light by the gaseous selenium in the sample chamber is represented by T (%), the absorbance is D and the concentration of the gaseous selenium is C, there are the following relationships:

$$T(\%) = I/I_o \times 100$$

$$D = \log(1/T(\%))$$

$$D \propto C$$

Figure 3:
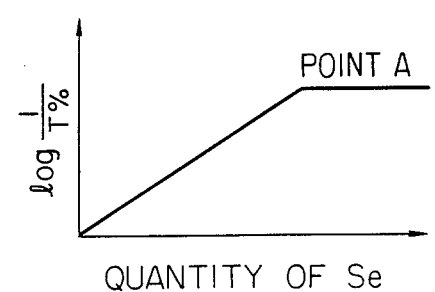
FIG. 3 is a graph showing the relationship between the quantity of selenium and log 1/T%.

On the other hand, it has been found that there is the relationship as shown in FIG. 3 between the weight of selenium and the absorbance D, i.e. log 1/T (%). Referring to FIG. 3, Point A represents a saturation point of selenium gas at a temperature of t, which is defined by the vapor pressure of selenium as shown in the following formula:

$$\log P(t) \text{ (mmHg)} = -4990/t + 8.09$$

wherein t is an absolute temperature.

For the purposes of detecting and quantitatively determining selenium or for controlling the quantity of selenium charged or for controlling the pressure of selenium, the method and monitor apparatus of the present invention can be applied with great advantages over various processes and apparatus used for the production of semiconductors or semiconductor devices using selenium. The present invention can also be applied with great advantage as a waste disposal apparatus, for example, an apparatus for the epitaxial growth of a compound semiconductors such as ZnSe, CdSe and the like (CVD furnaces, LPE furnaces, etc.) high pressure HB furnaces, annealing furnaces, selenium pressure annealing furnaces, MBE apparatus, MOCVD apparatus and melting furnaces of selenium-containing alloys, ceramics and glasses.

The advantages or merits of the present invention are summarized below.

(1) Since measurement is carried out using spectrum lines 1 to 16 shown in FIG. 3 near 335 nm or the highest peak at 335 nm by absorption of gaseous selenium, it is made possible to effect detection and quantitative determination of selenium at a temperature of lower than the atomizing temperature of selenium (higher than 2000° C.), which has hitherto been impossible in the prior art.

(2) Since the detection and quantitative determination can be carried out at a much lower temperature than in the prior art, as set forth above, in situ analysis is possible.

(3) Since simultaneous measurement is carried out for two or more peak wavelengths of the peaks 1 to 16 shown in FIG. 1, separation from other materials is clear and the quantitative determination of selenium is more accurate. Detection up to a concentration of 0.01 ppm is possible.

(4) The apparatus of the present invention can be used as a monitor apparatus for, in situ, detecting and quantitatively determining selenium and thereby controlling the quantity of selenium fed into the apparatus or the pressure of selenium.

EXAMPLES

The following examples are given in order to illustrate the present invention in detail without limiting the same.

Figure 4:
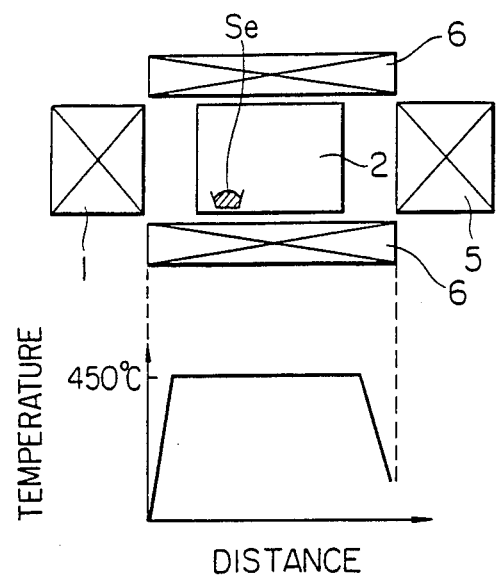
FIG. 4 is a schematic view of one embodiment of an apparatus for detecting and qantitatively determining selenium according to the present invention and a graph showing its temperature distribution.
Figure 5:
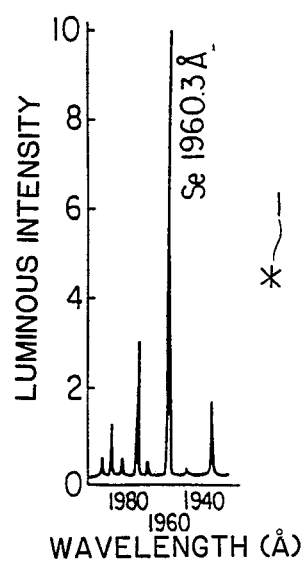
FIG. 5 is an atomic absorption spectrum of selenium.
Figure 6:
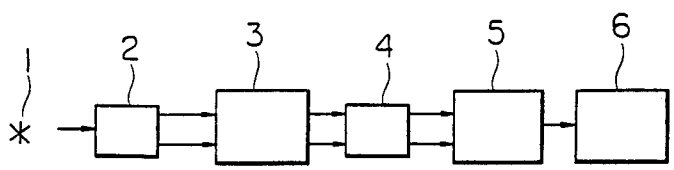
FIG. 6 is a schematic view of an apparatus used for an atomic absorption spectroscopic analysis.

Using an apparatus comprising sample chamber 2 provided with heater 6, as shown in FIG. 4, a sample containing selenium was charged in the chamber and held at a constant temperature of 450° C. to obtain an absorption spectrum as shown in FIG. 1. When various samples were subjected to measurement or analysis selecting two or more peaks from the peaks 1 to 16, quantitative determination of selenium in the order of 0.01 ppm was possible.

What is claimed is:

1. A method of detecting and quantitatively determining selenium, which comprises directing a spectrum line having a wavelength of 335 nm upon gaseous selenium at a temperature lower than the atomizing temperature of selenium, measuring the absorption of the spectrum line by the gaseous selenium and detecting and quantitatively determining selenium from the peak height of the intensity.

2. The method of claim 1, wherein the temperature which is lower than the atomizing temperature of selenium is within a temperature range of 220° to 1000° C.

3. The method of claim 1 in which the atomizing temperature of selenium is higher than 2000° C.

4. A method of detecting and quantitatively determining selenium, which comprises directing at least two spectrum lines having wavelengths selected from the group consisting of of 324 nm, 326 nm, 328 nm, 330 nm, 332.5 nm, 335 nm, 337.5 nm, 340 nm, 342 nm, 344.5 nm, 347 nm, 350 nm, 352.5 nm, 355 nm, 357.5 nm, and 360 nm upon gaseous selenium, at a temperature lower than the atomizing temperature of selenium measuring the absorption of the spectrum lines which has been absorbed by the gaseous selenium and detecting and quantitatively determining selenium from the peak heights of the intensity.

5. The method of claim 4, wherein the temperature which is lower than the atomizing temperature of the selenium is within a temperature range of 220° to 1000° C.

* * * * *